United States Patent [19]
Gordaliza et al.

[11] Patent Number: 5,739,114
[45] Date of Patent: Apr. 14, 1998

[54] IMMUNOSUPPRESSIVE CYCLOLIGNAN DERIVATIVES

[75] Inventors: Marina Gordaliza; Maria Angeles Castro; Arturo San Feliciano; Jose Maria Miguel del Corral; Maria Luisa Lopez, all of Salamanca; Glynn T. Faircloth, Madrid, all of Spain

[73] Assignee: Universidad de Salamanca, Salamanca, Spain

[21] Appl. No.: 558,127

[22] Filed: Nov. 13, 1995

[30] Foreign Application Priority Data

Nov. 14, 1994 [GB] United Kingdom ............... 9422947

[51] Int. Cl.⁶ ............... A61K 31/34; C07D 307/77; C07D 307/92
[52] U.S. Cl. ............... 514/22; 514/468; 549/299
[58] Field of Search ............... 514/22, 468; 549/299

[56] References Cited

U.S. PATENT DOCUMENTS 4,567,253   1/1986   Durst et al. ............... 536/18.1
4,644,072   2/1987   Vyas et al. ............... 549/433

FOREIGN PATENT DOCUMENTS

3612278 A1   10/1986   Germany.
WO 86/04062   7/1986   WIPO.

OTHER PUBLICATIONS

Hartwell and Schrecker, "The Chemistry of Podophyllum", *Progress in the Chemistry of Organic Natural Products*, pp. 84–166, 1957.

Terada et al., "Antitumor Agents. I. DNA Topoisomerase II Inhibitory Activity and the Structural Relationship of Podophyllotoxin Derivatives as Antitumor Agents", *Chem. Pharm. Bull.*, 40(10) 2720–2727, 1992.

Thurston et al., "Antitumor Agents. 78. Inhibition of Human DNA Topoisomerase II by Podophyllotoxin and α–Peltatin Analogues", *J. Med. Chem.*, 29:1547–1550, 1986.

Hansen et al., "New Compounds Related to Podophyllotoxin and Congeners: Synthesis, Structure Elucidation and Biological Testing", *Acta Chemica Scandinavica*, vol. 47 (1993), pp. 1190–1200.

Jones et al., "Synthesis of (±)–4–Deoxypodophyllotoxin, (±)–Podophyllotoxin and (±)–Epipodophyllotoxin", *Journal of the Chemical Society, Perkin Transactions 1*, Nov., 1993, pp. 2541–2548.

Buchardt et al., "Thermal Chemistry of Podophyllotoxin in Ethanol and a Comparison of the Cytostatic Activity of the Thermolysis Products", *Journal of Pharmaceutical Sciences*, vol. 75, No. 11, Nov. 1986, pp. 1076–1080.

Forsey et al., "Comprehensive Synthetic Route to Eight Diastereomeric Podophyllum Lignans", *The Journal of Organic Chemistry*, vol. 54, No. 18, 1 Sep. 1989, pp. 4280–4290.

Gordaliza et al., "Antineoplastic and antiviral activities of podophyllotoxin related lignans", *Chemical Abstracts*, vol. 120, No. 19, Abstract No. 120: 235425c. (May 9, 1994).

Gordaliza et al., "Antineoplastic and Antiviral Activities of Podophyllotoxin Related Lignans.", *Arch Pharm.*, vol. 327, No. 3, 1994, pp. 175–179.

Terada et al., "Antitumor Agents. I. DNA Topoisomerase II Inhibitory Activity and the Structure Relationship of Podophyllotoxin Derivatives as Antitumor Agents", *Chemical & Pharmaceutical Bulletin*, vol. 40, No. 10, Oct. 1992, pp. 2720–2727.

Thurston et al., "Antitumor Agents. 100. Inhibition of Human DNA Topoisomerase II by Cytotoxic Ether and Ester Derivatives of Podophyllotoxin and α–Peltatin", *Journal of Medical Chemistry*, vol. 32, No. 3, Mar. 1986, pp. 604–608.

*Primary Examiner*—Johann Richter
*Assistant Examiner*—Jane C. Oswecki
*Attorney, Agent, or Firm*—Ernest V. Linek

[57]   ABSTRACT

Immunosuppressive cyclolignan derivatives are provided of formula (I) or (II):

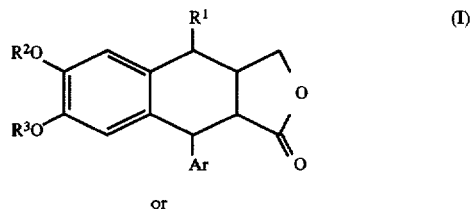

or

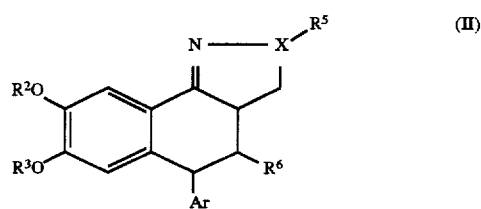

in which $R^1$ is hydrogen, hydroxy, alkoxy; $R^2$ and $R^3$ are hydrogen, alkyl, acyl, or together $R^2$ and $R^3$ form a group —$CHR^4$—; $R^4$ is hydrogen, alkyl, alkenyl, hydroxyalkyl, (poly)haloalkyl, aryl, acyloxyalkyl, alkoxy, carboxyalkyl, alkoxycarbonyl, carbamoyl; $R^5$ when present is hydrogen, alkyl, alkenyl, aryl, (poly)haloalkyl, acyl, carbamoyl, or thiocarbamoyl; $R^6$ is alkyl, hydroxyalkyl, haloalkyl, acyl, acyloxyalkyl, carboxy or alkoxycarbonyl; Ar is 3,4,5-trialkoxyphenyl or 4-hydroxy-3,5-dialkoxyphenyl; and X is nitrogen or oxygen.

5 Claims, No Drawings

IMMUNOSUPPRESSIVE CYCLOLIGNAN DERIVATIVES

This invention is concerned with cyclolignan derivatives, the preparation of such derivatives, and pharmaceutical compositions containing them.

It has now been found, in accordance with the present invention, that certain cyclolignan derivatives, as hereinafter defined, possess immunomodulatory activity, as evidenced by both the in vitro Mixed Lymphocyte Reaction (MLR) and the in vivo Graft-vs.-Host Reaction (GVHR) and Suppression Graft (SG) tests.

Accordingly, the invention provides cyclolignan derivatives of the formulae (I) and (II):

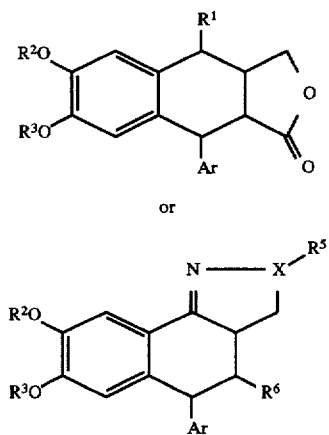

in which:

$R^1$ is hydrogen, hydroxy, alkoxy;

$R^2$ and $R^3$ are hydrogen, alkyl, acyl, or together $R^2$ and $R^3$ form a group —CHR$^4$—;

$R^4$ is hydrogen, alkyl, alkenyl, hydroxyalkyl, (poly) haloalkyl, aryl, acyloxyalkyl, alkoxy, carboxyalkyl, alkoxycarbonyl, carbamoyl;

$R^5$ when present is hydrogen, alkyl, alkenyl, aryl, (poly) haloalkyl, acyl, carbamoyl, or thiocarbamoyl;

$R^6$ is alkyl, hydroxyalkyl, haloalkyl, acyl, acyloxyalkyl, carboxy or alkoxycarbonyl;

Ar is 3,4,5-trialkoxyphenyl or 4-hydroxy-3,5-dialkoxyphenyl; and

X is nitrogen or oxygen.

PREFERRED EMBODIMENTS

The alkoxy groups preferably have from 1 to 6 carbon atoms, more preferably 1 to 4 carbon atoms. Examples include methoxy, ethoxy, propoxy, isopropoxy, butoxy, t-butoxy and other alkoxy groups.

The alkyl groups preferably have from 1 to 6 carbon atoms, more preferably 1 to 4 carbon atoms. Examples include methyl, ethyl, propyl, isopropyl, butyl, t-butyl and other alkyl groups.

The acyl groups preferably have from 1 to 20 carbon atoms, and more preferably are either short-chain acyl groups with 1 to 3 carbon atoms or long-chain acyl groups with 12 to 18 carbon atoms. The long chain acyl groups may be saturated or unsaturated, preferably of the kind occurring in natural fatty acids. Examples of acyl groups include formyl, acetyl or stearyl.

The alkenyl groups preferably have from 2 to 6 carbon atoms, more preferably 2 to 4 carbon atoms. Examples include vinyl or butenyl groups.

The hydroxyalkyl groups preferably have from 1 to 6 carbon atoms, more preferably 1 to 4 carbon atoms. Examples include hydroxymethyl, 1- or 2-hydroxyethyl or 3-hydroxypropyl and other hydroxyalkyl groups.

The haloalkyl and polyhaloalkyl groups preferably have from 1 to 6 carbon atoms, more preferably 1 to 4 carbon atoms, and preferably have a fluoro, chloro or bromo group. The (poly)haloalkyl groups are suitably monohalo or perhalo groups. Examples include chloromethyl or perfluomethyl groups.

The aryl group is preferably a phenyl or substituted phenyl group, suitably substituted with groups $R^4$ or $R^5$.

The preferred remaining possibilities for $R^4$, $R^5$ and $R^6$ follow the same general principles.

When $R^2$ and $R^3$ together form a group —CHR$^4$—, it is preferred that $R^4$ is an alkoxycarbonyl group.

The present compounds can exist as optical isomers, and the invention embraces the individual isomers and mixtures thereof, including the diastereomeric or racemic mix. The stereochemistry of the substituents may be selected as desired, and for example the groups $R^1$ and $R^6$ can be α or β.

More generally, the preferred compounds of this invention include compounds of formula (I), wherein the methylene group of the dioxolo moiety of podophyllium lignans has been removed or changed and the compounds of formula (II) with a fused imidazo or isoxazo ring.

Individual preferred compounds of this invention include

AP-37, which is 3,4-O-demethylenedeoxypicropodophyllin;

AP-39, which is 3,4-O-demethyleneepipodophyllotoxin;

AP-40, which is 3,4-O-demethylenepodophyllotoxin;

AP-47, which is 10-methoxycarbonyldeoxypicropodophyllin;

LL-4, which is methyl phenylpyrazopodophyllate; and

LL-11, which is isoxazopodophyllic acid.

Compounds of formula (I), and (II), as noted above, have immunomodulatory activity and, accordingly, the invention provides immunosuppressive pharmaceutical compositions comprising compounds of formula (I) or (II) as defined above in association with a pharmaceutical carder. Such pharmaceutical compositions may, for example, be adapted for oral, parenteral, or rectal administration by the incorporation or appropriate pharmaceutical carriers and options adjuvants. The invention also provides the use of cyclolignan derivatives of formula (I) and (II) in the manufacture of immunosuppressive compositions.

The immunosuppressive activity of various compounds in accordance with the invention is summarised below.

| | Immunosuppressive effects of several representative cyclolignans | | | |
|---|---|---|---|---|
| Compound | dose$^a$ | GVHR index$^b$ | SG index$^c$ | Cytotox.$^d$ |
| AP-37 | 0.1 | 58 | — | >20 |
| AP-39 | 1.5 | — | 200 | >10 |
| AP-40 | 1.5 | — | 229 | 0.5 |
| AP-47 | 10 | 56 | — | 2.5 |
| LL-4 | 1 | 53 | — | 1 |
| LL-11 | 0.15 | — | 204 | >10 |
| Cyclophosphamide | 200 | 79 | — | — |

-continued

Immunosuppressive effects of several representative cyclolignans

| Compound | dose[a] | GVHR index[b] | SG index[c] | Cytotox.[d] |
|---|---|---|---|---|
| Cyclosporin A | 25 | — | 178[*] | — |

[a] mg/kg/day (7 days)
[b] % reduction of spleen weight with respect to non treated animals.
[c] % of implant duration with respect to non treated animals.
[d] IC$_{50}$ (μg/ml) for monkey kidney fibroblasts.
[*] 20% of the animals died in this experiment before the end of the program (30 days of observation).

The compounds in accordance with the invention may be prepared from podophyllotoxin and analogues formula:

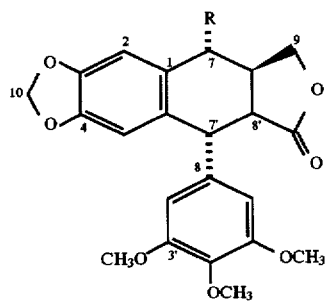

For example, see A.W. Fortschrite Chem. Org. Naturstoff 15.83 (1953) which describes podophyllotoxin where R is hydroxy and 8'—H is β; deoxypodophyllotoxin where R is hydrogen and 8'—H is β; and deoxypicropodophyllin where R is hydrogen and 8'—H is α. See also J. Med. Chem. 29 1547–1550 (1986) and Chem. Pharm. Bull. 40 2720–2727 (1992).

For example, compounds of this invention can be made in accordance with the following reaction scheme, where partial structures are shown as appropriate:

where reaction a) is esterification and/or reduction and/or acylation and/or oxidation in the adequate sequence and combination.

Other equivalent reaction conditions can be employed.

EXAMPLES OF THE INVENTION

In order that the invention may be further understood, the following examples are given by way of illustration only.

EXAMPLE 1

Preparation of AP-37:

To a solution of boron trichloride in $CH_2Cl_2$(1M, 2 ml) precooled at −70° to −65° was added dropwise deoxypicropodophyllin (100 mg) in dry $CH_2Cl_2$(6 ml). After stirring at the same temperature for an additional 1 hour, the mixture was poured into ice-water and extracted with ethyl acetate. The residue obtained after evaporating the organic solvent was dissolved in a mixture of water:acetone:calcium carbonate (3 ml:3 ml: 1 g) and refluxed for 1 hour. The suspension was acidified with 2N HCl and extracted with ethyl acetate. Evaporation of the solvent afforded 80 mg of AP-37.

[M+]:386 mp:226°–228° C. (MeOH) [α]$_D$(CHCl$_3$):+ 46.8° UV λ$_{max}$(EtOH)(ε):222(23300), 288(7200) IR (KBr): 3400,1740,1600,1510,1300,1110 cm$^{-1}$.

EXAMPLE 2

Preparation of AP-47:

A mixture of AP-37 (50 mg), methyl dichloroacetate (0.06 ml) and anhydrous K$_2$CO$_3$(100 mg) in DMF (2 ml) was stirred at 90°–100° C. under argon for 2 hours. After cooling the mixture, water (3 ml) was added and stirred again at 90°–100° C. for 40 min. then acidified with 2N HCl, basified with saturated NaHCO$_3$ and extracted with ethyl acetate. The aqueous layer was acidified with 2N HCl and extracted with EtOAc. Evaporation of the solvent afforded 40 mg of AP-47.

mp: 95°–98° C. (MeOH/CH$_2$Cl$_2$) [α]$_D$(CHCl$_3$):+20.6° UV λ$_{max}$(EtOH)(ε):214(20500), 290(3600) IR (CHCl$_3$): 3010,1770,1600,1500,1480,1220,1140 cm$^{-1}$.

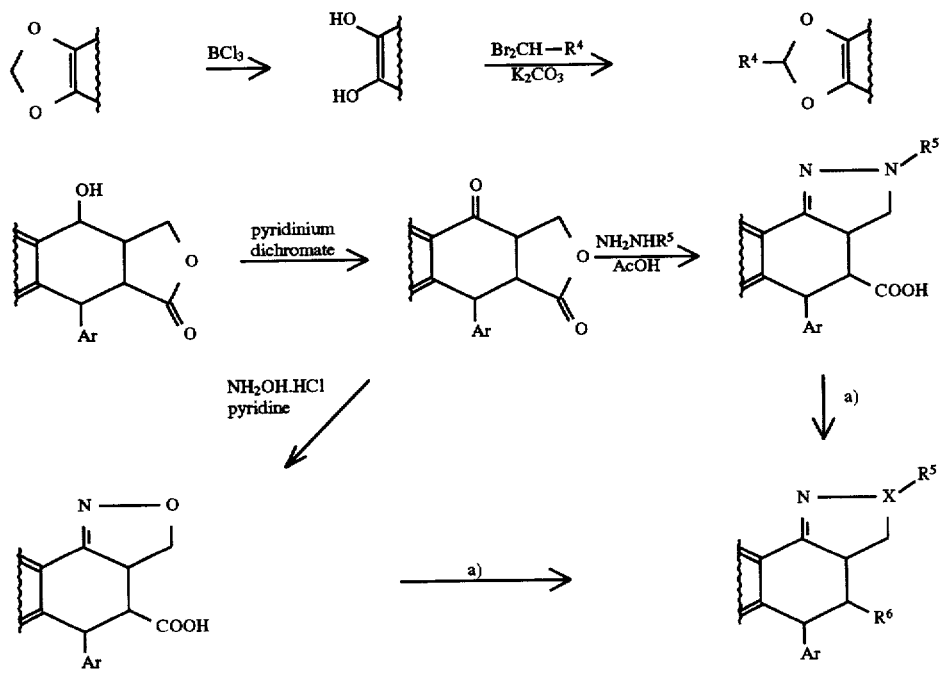

EXAMPLE 3

Preparation of LL-11

0.2 ml of pyridine and 64 mg of hydroxylamine hydrochloride were added to a solution of 300 mg of podophyllotoxone in 15 ml of ethanol. The reaction mixture was stirred at 95° C. for 72 h. Then it was concentrated under vacuum and extracted with ethyl acetate. The reaction product was purified by flash chromatography to provide 250 mg of LL-11.

[M+]:428 mp:246°–248° C.(CH$_2$Cl$_2$) [α]$_D$(CHCl$_3$):– 152.6° UV λ$_{max}$(EtOH)(ε):215(26500),274(12000),313 (8900). IR(KBr):3600,–2700,1700,1600,1510,1240,1130 cm$^{-1}$.

We claim:

1. A compound of the formula (I):

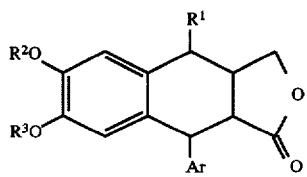

(I)

wherein:

R$^1$ is hydrogen or hydroxy;

R$^2$ and R$^3$ are hydrogen;

and

Ar is 3,4,5-trialkyoxyphenyl.

2. The compound of claim 1, which is 3,4-O-demethylenedeoxy-picropodophyllin.

3. The compound of claim 1, which is 3,4-O-demethylene-epipodophyllotoxin.

4. The compound of claim 1, which is 3,4-O-demethylene-podophyllotoxin.

5. A pharmaceutical composition that comprises an effective immunosuppressive amount of a compound as defined any of claims 1–4 together with a pharmaceutically acceptable carrier.

* * * * *

(12) EX PARTE REEXAMINATION CERTIFICATE (5597th)
United States Patent
Gordallza et al.

(10) Number: US 5,739,114 C1
(45) Certificate Issued: Nov. 7, 2006

(54) IMMUNOSUPPRESSIVE CYCLOLIGNAN DERIVATIVES

(75) Inventors: Marina Gordallza, Salamanca (ES); Maria Angeles Castro, Salamanca (ES); Arturo San Feliciano, Salamanca (ES); Jose Maria Miguel del Corral, Salamanca (ES); Maria Luisa Lopez, Salamanca (ES); Glynn T. Faircloth, Madrid (ES)

(73) Assignee: Universidad de Salamanca, Salamanca (ES)

Reexamination Request:
No. 90/006,357, Aug. 16, 2002

Reexamination Certificate for:
Patent No.: 5,739,114
Issued: Apr. 14, 1998
Appl. No.: 08/558,127
Filed: Nov. 13, 1995

(30) Foreign Application Priority Data

Nov. 14, 1994 (GB) .............................................. 9422947

(51) Int. Cl.
  A61K 31/34 (2006.01)
  C07D 307/77 (2006.01)
  C07D 307/92 (2006.01)

(52) U.S. Cl. ......................... 514/22; 514/468; 549/299
(58) Field of Classification Search .................. 514/22, 514/468; 549/299
  See application file for complete search history.

(56) References Cited

U.S. PATENT DOCUMENTS 5,120,862 A * 6/1992 Vyas et al. ...................... 549/31
5,541,223 A * 7/1996 Lee et al. ...................... 514/468
5,776,962 A * 7/1998 Gross et al. ................. 514/359
5,962,516 A * 10/1999 Qi et al. ...................... 514/468
6,255,339 B1 * 7/2001 Kurihara et al. ............ 514/468

FOREIGN PATENT DOCUMENTS

WO    WO 86/04062    7/1986

OTHER PUBLICATIONS

Descotes, Jacques, Immunotoxicology, Drug Safety 2005: 28(2): 127–136.*
Perspective Diagnosis, Treatment, and Prevention of Selected common HIV–Related Opportunistic Infections in the Caqribbean Region, Top HIV Med. 2004; 12(5); 136–141.*

Reference D11 from EP Application No. 95308102.3—E. Schreier: 165. On the Structure of Sikkimotoxins II. Partial Synthesis of the 6,7–Dimethoxy Analogs of Podophyllotoxin, Epi–, Neo– and Deoxypodophyllotoxin, *Helvetica Chimica Acta*, vol. 47, Fascicle 6, No. 164–165, 1964, pp. 1529–1555 (translated pp. 1529 and 1532–1533).

Reference D12 from EP Application No. 95308102.3—E. Schreier: 9. On the Structure of Sikkimotoxin I. Synthesis Stereoisomeric 6,7–Dimethoxy Analogs of Podophyllotoxin, *Helvetica Chimica Acta*, vol. 46, Fascicle 1, No. 9, 1963, pp. 75–115 (translated pp. 75 and 96–97).

Reference D9 from EP Application No. 95308102.3—T. Terada et al., *Chem. Pharm. Bull.*, vol. 40, No. 10, pp. 2720–2727 (1992).

* cited by examiner

*Primary Examiner*—Joseph K. McKane

(57) ABSTRACT

Immunosuppressive cyclolignan derivatives are provided of formula (I) or (II):

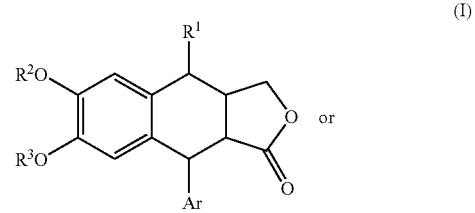

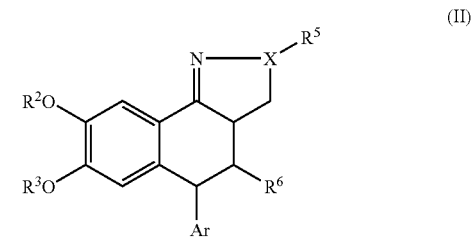

in which $R^1$ is hydrogen, hydroxy, alkoxy; $R^2$ and $R^3$ are hydrogen, alkyl, acyl, or together $R^2$ and $R^3$ form a group —$CHR^4$—; $R^4$ is hydrogen, alkyl, alkenyl, hydroxyalkyl, (poly)haloalkyl, aryl, acyloxyalkyl, alkoxy, carboxyalkyl, alkoxycarbonyl, carbamoyl; $R^5$ when present is hydrogen, alkyl, alkenyl, aryl, (poly)haloalkyl, acyl, carbamoyl, or thiocarbamoyl; $R^6$ is alkyl, hydroxyalkyl, haloalkyl, acyl, acyloxyalkyl, carboxy or alkoxycarbonyl; Ar is 3,4,5-trialkoxyphenyl or 4-hydroxy-3,5-dialkoxyphenyl; and X is nitrogen or oxygen.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–5 are cancelled.

* * * * *